(12) United States Patent
Bar-Tal

(10) Patent No.: US 8,926,511 B2
(45) Date of Patent: Jan. 6, 2015

(54) LOCATION SYSTEM WITH VIRTUAL TOUCH SCREEN

(75) Inventor: Meir Bar-Tal, Zichron Ya'acov (IL)

(73) Assignee: Biosense Webster, Inc., Diamond Bar, CA (US)

( * ) Notice: Subject to any disclaimer, the term of this patent is extended or adjusted under 35 U.S.C. 154(b) by 1363 days.

(21) Appl. No.: 12/039,779

(22) Filed: Feb. 29, 2008

(65) Prior Publication Data

US 2009/0221907 A1    Sep. 3, 2009

(51) Int. Cl.
*A61B 8/00*    (2006.01)
*A61B 5/06*    (2006.01)

(52) U.S. Cl.
CPC .. *A61B 5/06* (2013.01); *A61B 5/064* (2013.01)
USPC ........................................................ 600/443

(58) Field of Classification Search
USPC ......... 600/424, 437, 443–447, 454–456, 458; 128/916; 382/128
See application file for complete search history.

(56) References Cited

U.S. PATENT DOCUMENTS

| | | | |
|---|---|---|---|
| 5,417,210 A * | 5/1995 | Funda et al. | 600/425 |
| 5,729,129 A * | 3/1998 | Acker | 324/207.12 |
| 5,913,820 A * | 6/1999 | Bladen et al. | 600/407 |
| 6,129,668 A | 10/2000 | Haynor et al. | |
| 6,201,387 B1 | 3/2001 | Govari | |
| 6,332,089 B1 | 12/2001 | Acker et al. | |
| 6,427,079 B1 | 7/2002 | Schneider et al. | |
| 6,618,612 B1 | 9/2003 | Acker et al. | |
| 6,690,963 B2 | 2/2004 | Ben-Haim et al. | |
| 6,695,779 B2 | 2/2004 | Sauer et al. | |
| 7,174,201 B2 | 2/2007 | Govari et al. | |
| 7,285,117 B2 * | 10/2007 | Krueger et al. | 606/34 |

(Continued)

FOREIGN PATENT DOCUMENTS

| | | |
|---|---|---|
| JP | 03/520062 A1 | 11/2000 |
| JP | 04/533863 A2 | 8/2002 |
| WO | WO 2006/051523 A2 | 5/2006 |
| WO | WO 2006/054207 | 5/2006 |

OTHER PUBLICATIONS

EP Partial Search Report No. EP 09 25 0552 dated Jun. 8, 2009.

(Continued)

*Primary Examiner* — Elmer Chao
(74) *Attorney, Agent, or Firm* — Louis J. Capezzuto (57) ABSTRACT

Control of an invasive medical instrument during a medical procedure is achieved using a system that includes magnetic field-based location facilities. Magnetic field sensors are placed in a medical instrument, e.g., a probe, and in an interface device to enable respective positions of the probe and the interface device to be ascertained by a location processor when the sensors are exposed to a magnetic field. The interface device is disposed such that an operator can control the medical instrument and the interface device concurrently. A display device, which can comprise a virtual reality display, is responsive to movements of the interface device as determined by the location processor to control the medical instrument, invoke various functions of the system, e.g., image manipulation, and otherwise facilitate the medical procedure via a graphical user interface.

11 Claims, 6 Drawing Sheets

(56) References Cited

U.S. PATENT DOCUMENTS

| | | | |
|---|---|---|---|
| 7,697,973 B2* | 4/2010 | Strommer et al. | 600/424 |
| 2002/0049375 A1 | 4/2002 | Strommer et al. | |
| 2004/0068178 A1 | 4/2004 | Govari | |
| 2004/0147920 A1 | 7/2004 | Keidar | |
| 2004/0193006 A1 | 9/2004 | Chen et al. | |
| 2004/0267125 A1* | 12/2004 | Skyba et al. | 600/443 |
| 2005/0099290 A1 | 5/2005 | Govari | |
| 2006/0100505 A1* | 5/2006 | Viswanathan | 600/424 |
| 2006/0241445 A1 | 10/2006 | Altmann et al. | |
| 2009/0080738 A1* | 3/2009 | Zur et al. | 382/131 |

OTHER PUBLICATIONS

Bajura M et al.: Merging Virtual Objects With Real World: Seeing Ultrasound Imagery Within the Patient, Computer Graphics, vol. 26, No. 2, Jul. 1992.

Bajura, M. et al. Merging Virtual Objects With the Real World: Seeing Ultrasound Imagery Within the Patient. Computer Graphics, (Jul. 26, 1992), No. 2, pp. 203-210.

CN 200910130767.5 OA Jun. 9, 2014.

JP 2009-045364 OA May 7, 2013.

* cited by examiner

LOCATION SYSTEM WITH VIRTUAL TOUCH SCREEN

BACKGROUND OF THE INVENTION

1. Field of the Invention

This invention relates to systems for invasive medical procedures. More particularly, this invention relates to using magnetic fields to track a medical instrument within a living body.

2. Description of the Related Art

Magnetic tracking systems for medical application use magnetic fields to detect locations both of points in the patient's body and of invasive devices, such as catheters and surgical tools, that are in proximity to or inside the body. For this purpose, a magnetic field generator produces a field in and around an area of the body, and sensors in the body and in the invasive device detect the field. A system console receives the sensor signals and displays the location of the invasive device relative to the body.

For example, commonly assigned U.S. Pat. No. 7,174,201, issued to Govari, et al., and which is herein incorporated by reference, discloses apparatus for performing a medical procedure within a subject, which includes a wireless tag fixed to the tissue and which includes a first sensor coil. A second sensor coil is fixed to a medical device for use in performing the procedure. An integral processing and display unit includes a plurality of radiator coils, along with processing circuitry and a display. The radiator coils generate electromagnetic fields in a vicinity of the tissue, thereby causing currents to flow in the sensor coils. The processing circuitry processes the currents to determine coordinates of the tag relative to the medical device. The display is driven by the processing circuitry so as to present a visual indication to an operator of the medical device of an orientation of the device relative to the tag.

U.S. Pat. No. 5,913,820, issued to Bladen, et al., and which is herein incorporated by reference, discloses methods and apparatus for locating the position, preferably in three dimensions, of a sensor by generating magnetic fields, which are detected at the sensor. The magnetic fields are generated from a plurality of locations and, in one embodiment of the invention, enable both the orientation and location of a single coil sensor to be determined. The system allows an operator to wear small, single coil sensors about his body to enable his movements to be detected and interpreted by a machine without requiring physical contact between the operator and the machine. For example, the positioning system could enable an operator to interact with images on a television or computer screen without the use of a conventional keyboard, mouse or stylus.

U.S. Pat. No. 6,129,668, issued to Haynor et al., and which is herein incorporated by reference, discloses a device to detect the location of a magnet coupled to an indwelling medical device within a patient using three or more sets of magnetic sensors each having sensor elements arranged in a known fashion. Each sensor element senses the magnetic field strength generated by the magnet and provides data indicative of the direction of the magnet in a three-dimensional space.

U.S. Pat. No. 6,427,079, issued to Schneider, et al., and which is herein incorporated by reference, discloses a remote location determination system that uses splines of magnetic field values to determine location parameters. The location determination system is used on a laser catheter that is operable to perform myocardial revascularization. An automatic calibration technique compensates for any variations in gain in a sensor and related components. Methods for reducing the effects of eddy currents in surrounding conductive objects are used in electromagnetic position and orientation measurement systems.

SUMMARY OF THE INVENTION

In systems such as the one disclosed in the above-noted U.S. Pat. No. 7,174,201, in order to interact with the console, the system operator, such as a physician, must generally use a conventional user interface device, e.g., a keyboard, mouse or touch screen. The operator may have to disengage from manipulating the invasive device, and move to a different position to work the user interface. Alternatively, he must instruct an assistant to take the necessary actions.

Embodiments of the present invention provide new methods and devices for user interaction with a system for medical treatment and/or diagnosis that uses magnetic position tracking. These methods and devices permit the system operator to interact with the console without leaving his normal operating position. In some of these embodiments, the operator is provided with a stylus or other user interface device containing a magnetic sensor, which is linked to the console. The interface device may itself have a dual function as an invasive medical instrument. As long as the stylus is near the patient's body, the sensor senses the fields generated by the magnetic field generator. In other embodiments, the interface device and the medical instrument generate magnetic fields, which are sensed by an external position sensor. A position processor in the console is thus able to determine the location of the stylus just as it determines the locations of the other elements of the system. The system console displays a cursor on a screen, which moves as the operator moves the stylus. The operator can use this cursor to actuate on-screen controls, to draw lines on the screen, and to mark points and otherwise interact with images and maps that are displayed on the screen.

In other words, the effect of the stylus and magnetic tracking system is to provide a "virtual touch screen" that the system operator can use conveniently while operating on the patient.

Some embodiments of the present invention permit the system operator to view a virtual image of an anatomical structure, in the actual location of the structure, using a "virtual reality" or "augmented reality" display, and to use the stylus to interact with the image. For example, the display with which the operator interacts using the stylus may be presented on goggles worn by the system operator. The goggles contain a position sensor, so that the display is registered with the body of the patient.

An embodiment of the invention provides apparatus for invasive medical operations in the body of a living subject. The apparatus includes one or more field generating elements disposed at known locations for generating magnetic fields at respective frequencies, and a medical instrument adapted for insertion into the body. The medical instrument has a first magnetic position sensor coupled thereto that emits first signals responsively to the magnetic fields. An interface device has a second magnetic position sensor coupled thereto that emits second signals responsively to the magnetic fields. The apparatus includes a position processor operative to receive the first signals and the second signals and to determine respective positions of the interface device and the medical instrument relative to the known locations, responsively to the first signals and the second signals, and a display device operative to display an image responsively to the position of the medical instrument. The display device has a cursor moveable thereon under control of the position processor responsively to changes in the position of the interface device.

According to an aspect of the apparatus, the display device has a display control that is actuated responsively to a superimposition of the cursor thereon.

According to another aspect of the apparatus, the display device has a display control that is actuated responsively to a displacement of the interface device generally toward the display device while the cursor is superimposed on the display control.

According to one aspect of the apparatus, the display device is a virtual reality display device having a third magnetic position sensor that emits third signals responsively to the magnetic fields.

In yet another aspect of the apparatus, positioning controls are provided for the medical instrument, and the interface device is disposed within reach of an operator of the positioning controls.

According to a further aspect of the apparatus, the first magnetic position sensor and the second magnetic position sensor comprise at least two sensor coils.

Other embodiments of the invention provide methods that are carried out by the above-described apparatus.

BRIEF DESCRIPTION OF THE DRAWINGS

For a better understanding of the present invention, reference is made to the detailed description of the invention, by way of example, which is to be read in conjunction with the following drawings, wherein like elements are given like reference numerals, and wherein.

DETAILED DESCRIPTION OF THE INVENTION

In the following description, numerous specific details are set forth in order to provide a thorough understanding of the present invention. It will be apparent to one skilled in the art, however, that the present invention may be practiced without these specific details. In other instances, well-known circuits, control logic, and the details of computer program instructions for conventional algorithms and processes have not been shown in detail in order not to obscure the present invention unnecessarily.

Software programming code, which embodies aspects of the present invention, is typically maintained in permanent storage, such as a computer readable medium. In a client/server environment, such software programming code may be stored on a client or a server. The software programming code may be embodied on any of a variety of known media for use with a data processing system, such as a diskette, or hard drive, or CD-ROM. The code may be distributed on such media, or may be distributed to users from the memory or storage of one computer system over a network of some type to other computer systems for use by users of such other systems.

Figure 1:
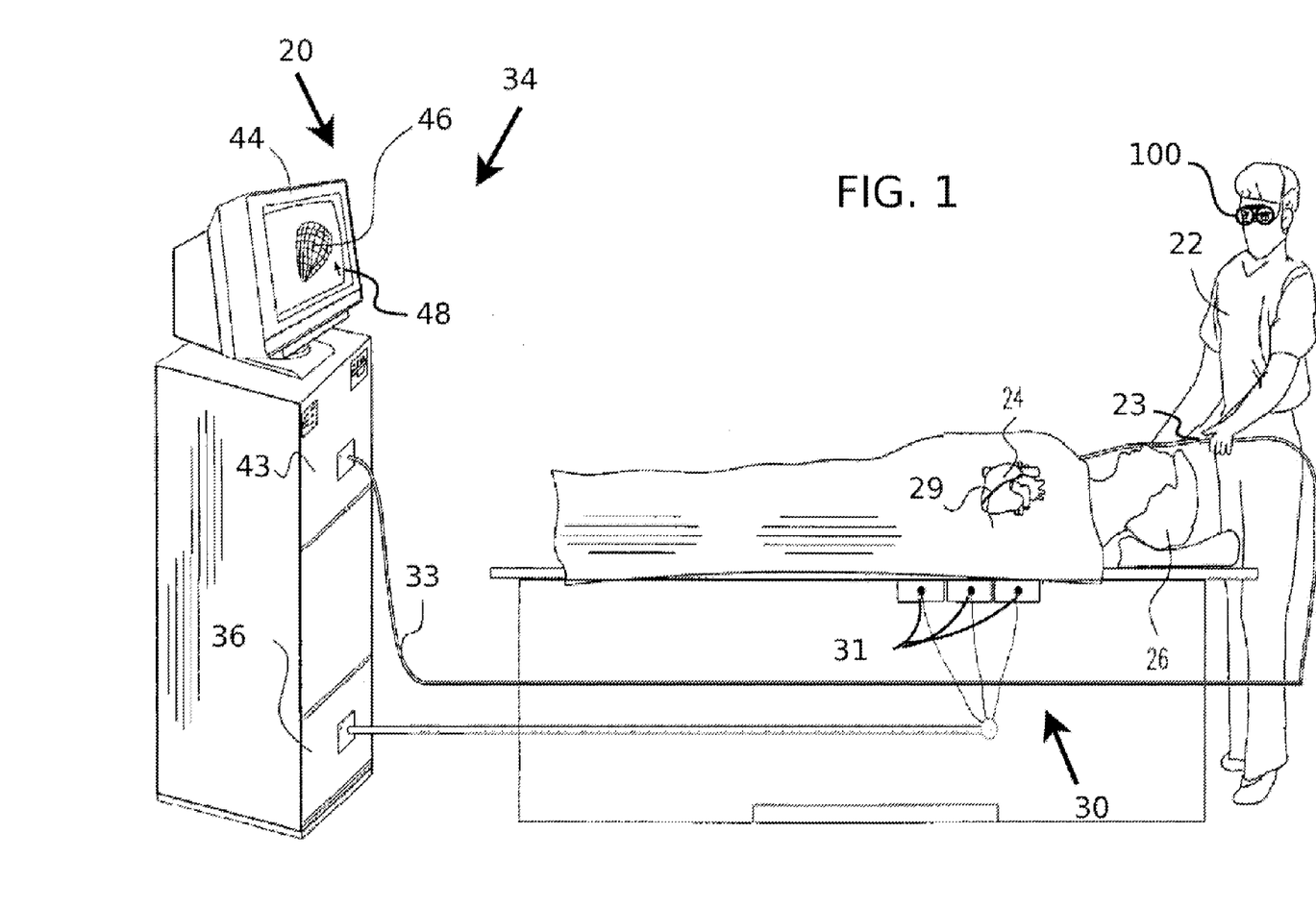
FIG. 1 is a pictorial illustration of a system for medical imaging using a virtual touch screen, in accordance with a disclosed embodiment of the invention.

Turning now to the drawings, reference is initially made to FIG. 1, which is a pictorial illustration of a system 20 that tracks and operates a medical instrument within a living body using a virtual touch screen, which is constructed and operative in accordance with a disclosed embodiment of the invention. An operator, for example a physician 22 may use system 20 to obtain medical images using a probe, such as a catheter 23, which may be inserted into an internal body cavity, such as a chamber of a heart 24 of a subject 26. Typically, catheter 23 is used for diagnostic or therapeutic medical procedures, such as mapping electrical potentials in the heart or performing ablation of heart tissue. The catheter or other intra-body device may alternatively be used for other purposes, by itself or in conjunction with other treatment devices. The cardiac application described with respect to FIG. 1 is exemplary. The principles of the invention are applicable to many invasive medical and surgical procedures throughout the body.

Figure 2:
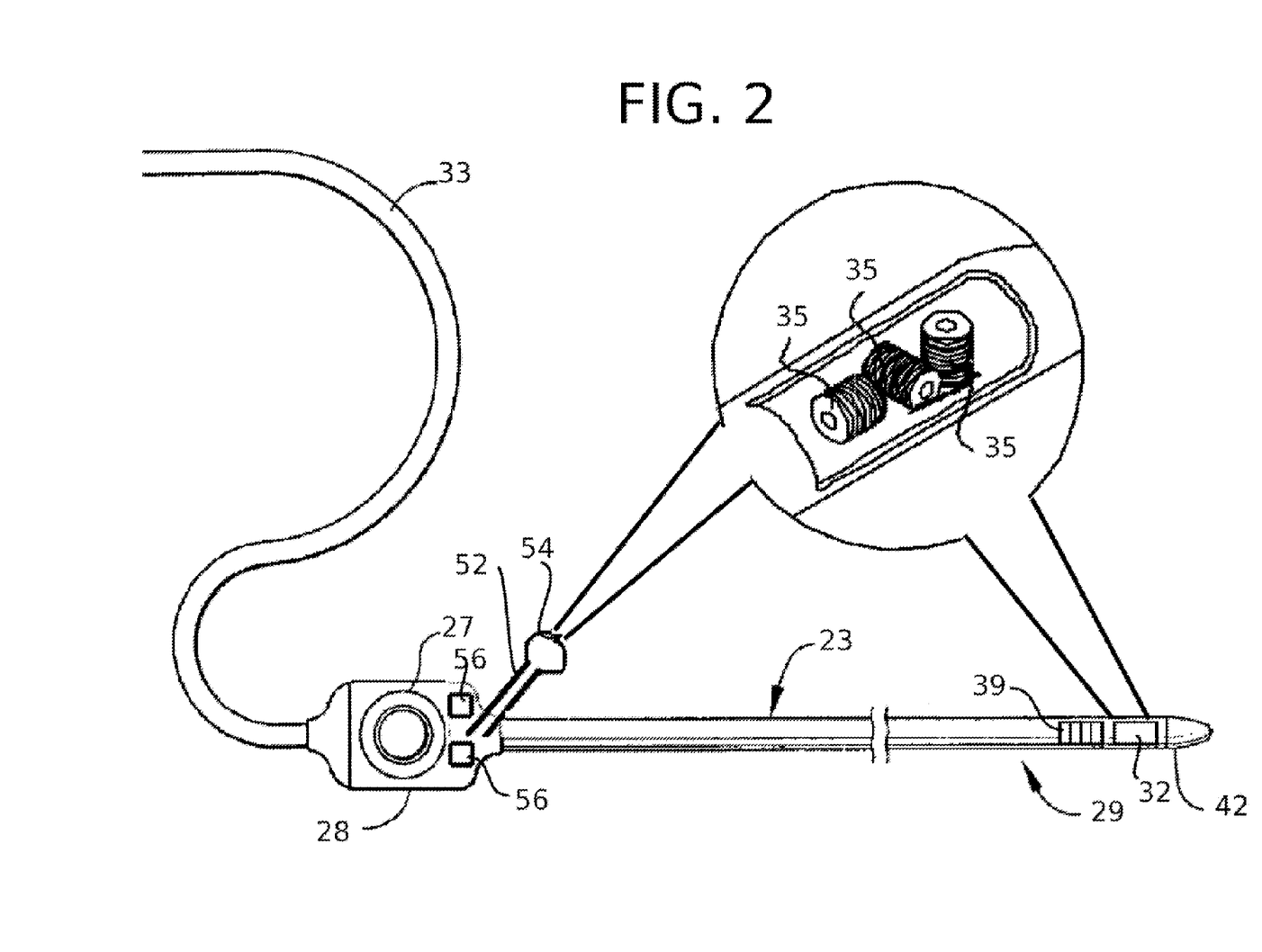
FIG. 2 is a pictorial illustration of a catheter that may be used in the system shown in FIG. 1, in accordance with an embodiment of the present invention.

Reference is now made to FIG. 2, which is a pictorial illustration of catheter 23, in accordance with an embodiment of the present invention. The catheter shown is exemplary; many other types of catheters may be used as catheter 23. Catheter 23 typically comprises positioning controls 27 on a handle 28 to enable the physician to steer, locate and orient, and operate a distal end 29 of catheter 23 as desired.

A pointing device, e.g., joystick 52 is attached to handle 28. In some embodiments, handle 28 comprises one or more touch-activated switches, shown as buttons 56. Alternatively, buttons 56 may be located on joystick 52. Joystick 52 and buttons 56 are used for controlling system 20, as described in detail herein below.

Distal end 29 and joystick 52 include position sensors 32 and 54 respectively, each comprising sensor coils 35 as described herein below.

In some embodiments, distal end 29 comprises an ultrasonic imaging sensor 39. Ultrasonic imaging sensor 39 typically transmits a short burst of ultrasound energy and converts the reflected ultrasound into electrical signals, which are transmitted via cables 33 to console 34 (FIG. 1), as is known in the art.

In some embodiments, distal end 29 also comprises at least one electrode 42 for performing diagnostic functions, therapeutic functions, or both, such as electro-physiological mapping and radiofrequency (RF) ablation. In one embodiment, electrode 42 is used for sensing local electrical potentials. The electrical potentials measured by electrode 42 may be used in mapping the local electrical activity on the endocardial surface. When electrode 42 is brought into contact or proximity with a point on the inner surface of heart 24 (FIG. 1), the electrode measures the local electrical potential at that point. The measured potentials are converted into electrical signals and sent through catheter 23 to an image processor 43 (FIG. 1), which converts the signals into an electro-anatomical map.

Alternatively, electrode 42 may be used to measure parameters different from the electrical potentials described above, such as various tissue characteristics, temperature, and blood flow.

Referring again to FIG. 1, system 20 comprises a positioning subsystem 30 that measures location and orientation coordinates of distal end 29 of catheter 23. As used herein, the term "location" refers to the spatial coordinates of an object, the term "orientation" refers to angular coordinates of the object, and the term "position" refers to the full positional information of the object, comprising both location and orientation coordinates.

In one embodiment, positioning subsystem 30 comprises a magnetic position tracking system that determines the position of distal end 29 of catheter 23. Positioning subsystem 30 typically comprises a set of external radiators, such as field generating elements, e.g., coils 31, which are in fixed, known locations external to the subject. Coils 31 generate fields, typically magnetic fields, in the vicinity of heart 24.

Referring again to FIG. 2, position sensor 32 senses the fields generated by coils 31 and transmits, in response to the sensed fields, position-related electrical signals over cables 33 running through catheter 23 to console 34 (FIG. 1). Alternatively, position sensor 32 may transmit signals to the console over a wireless link.

In order to determine six positional coordinates (X, Y, Z directions and pitch yaw and roll orientations), position sensor 32 comprises at least two, and preferably three, sensor coils 35, adapted to the frequency of one of coils 31 as is known in the art. Sensor coils 35 are wound on either air cores or cores of material. The axes of sensor coils 35 should be non-parallel and preferably mutually orthogonal.

In some applications, where fewer position coordinates are required, only a single sensor coil 35 may be necessary in position sensor 32.

Position sensor 54, which is located in the joystick 52, preferably in the handle, is similar to position sensor 32. Position sensor 54 senses the fields generated by coils 31, and is used to determine the position of the handle of joystick 52 including its angular orientation in space. Position sensor 54 requires at least one sensing coil, and preferably has three coils.

Referring again to FIG. 1, console 34 comprises a position processor 36 that calculates the location and orientation of distal end 29 of catheter 23 based on the signals sent by position sensor 32 (FIG. 2). Position processor 36 typically receives, amplifies, filters, digitizes, and otherwise processes signals from catheter 23. System 20 and position processor 36 may also be realized as elements of the CARTO XP EP Navigation and Ablation System, available from Biosense Webster, Inc., 3333 Diamond Canyon Road, Diamond Bar, Calif. 91765, and suitably modified to execute the principles of the pre-sent invention.

Some position tracking systems that may be used in embodiments of the present invention are described, for example, in U.S. Pat. Nos. 6,690,963, 6,618,612 and 6,332,089, and U.S. Patent Application Publications 2004/0147920 and 2004/0068178, all of which are incorporated herein by reference.

In some embodiments, image processor 43 uses the electrical signals received from ultrasonic imaging sensor 39 (FIG. 2) and positional information received from position sensor 32 in distal end 29 of catheter 23 to produce an image of a target structure of the subject's heart. The images may be enhanced using electrical information derived from electrode 42.

In other embodiments, image processor 43 may not produce a medical image, but may merely produce an image of distal end 29 of catheter 23 overlaid on a representation of subject 26, or may simply show the position of distal end 29 with respect to a target within the subject, in order to assist physician 22 with a medical procedure.

Images produced by image processor 43 are output on a display device 44. For example, FIG. 1 shows an image 46 of part of heart 24. System 20 typically provides display controls, for example a GUI (Graphical User Interface), comprising windows, icons and menus, for manipulating and viewing images produced by image processor 43. An interface device is used to move a cursor 48 on display device 44.

In one embodiment the interface device comprises joystick 52 (FIG. 2), which is within reach of physician 22 when he is using operating controls 27. For example, in a medical procedure involving realtime image processing, rotation of the joystick may continuously control a parameter such as the edge threshold in an edge detection algorithm. Other joystick motions and button commands may be user-assigned in order to control other aspects of the operation of the system 20. As physician 22 moves joystick 52, the location of position sensor 54 is tracked by the position processor 36 (FIG. 1) transmitted to console 34, where it is registered on the display 44. The position processor 36 translates joystick movements into movements of cursor 48 on display device 44.

Figure 3:
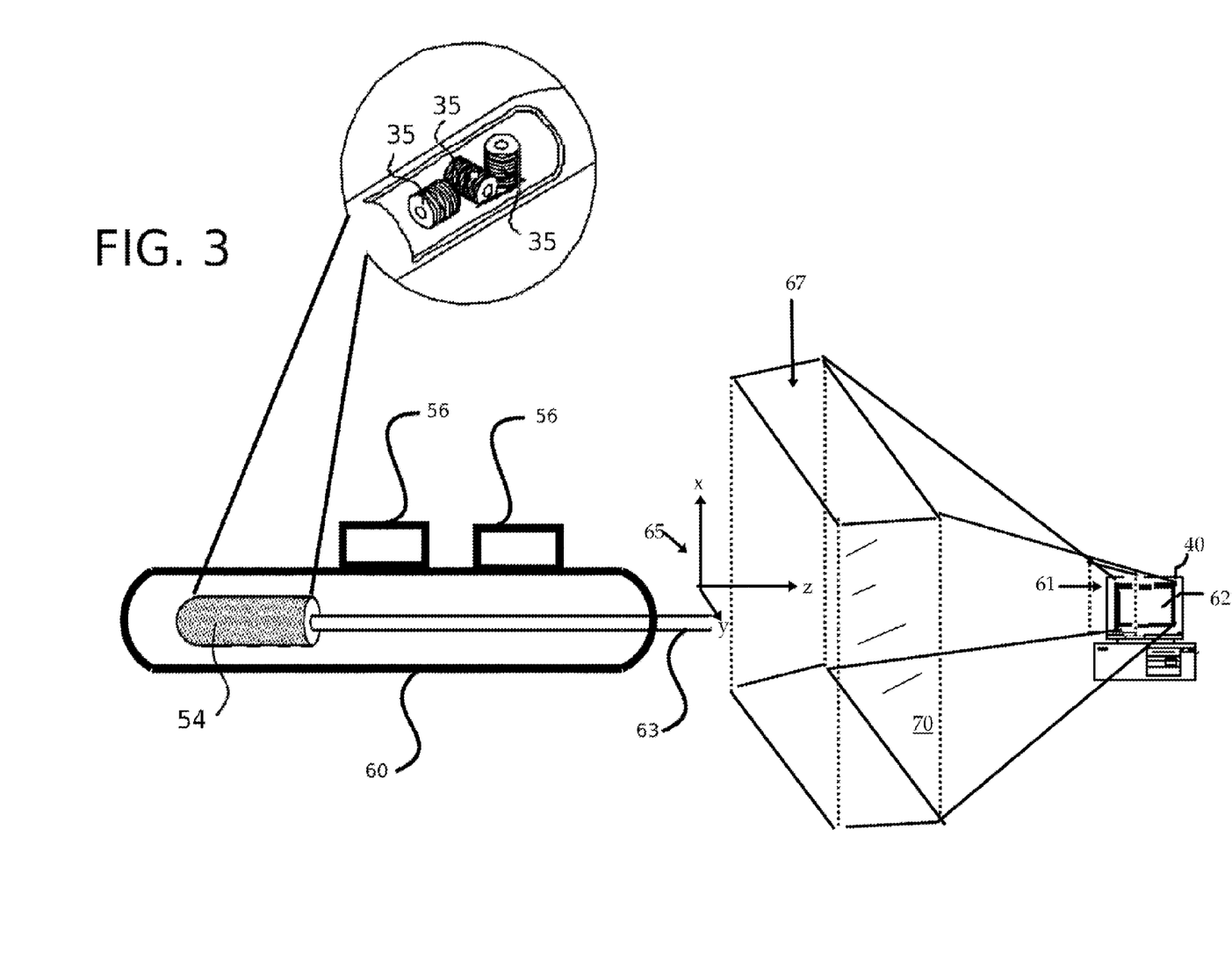
FIG. 3 is a pictorial illustration of an interface device that may be used in the system shown in FIG. 1, in accordance with an alternate embodiment of the invention.

Alternatively, the interface device may be a separate device, distinct from catheter 23 or any other medical device. Reference is now made to FIG. 3, which is a diagram of an exemplary interface device 60 for use with system 20 (FIG. 1), in accordance with an alternate embodiment of the invention. Interface device 60 may be a wand or stylus, and is shaped to be easily graspable and manipulable by physician 22 (FIG. 1). Interface device 60 comprises position sensor 54 and buttons 56, as described above. Position sensor 54 senses magnetic fields produced by coils 31 (FIG. 1) and transmits, in response to the sensed fields, position-related electrical signals over cables 63 to console 34. Alternatively, position sensor 54 may transmit signals to the console over a wireless link. In this way, system 20 is able to determine the position of interface device 60.

A 3-dimensional spatial region 61 including screen 62 of display 40 is mapped by the position processor 36 to a spatial region 67 near or including device 60. A displacement of device 60 in the region 67 that changes its XY coordinates in coordinate system 65 produces a corresponding movement of a cursor on the screen 62. When the device 60 is displaced so as to change its Z-coordinate and intersect virtual plane 70, physical contact with the screen 62 is emulated. This event stimulates the graphical user interface of the display 40 as though a physical touch screen were contacted at a point corresponding to the XY coordinate of the intersection in the plane 70.

Icons and menus (not shown) on the display 40 are actuated by superimposing the cursor on them. In an alternate embodiment, the icons and menus are actuated by passing the cursor over them while pressing one of buttons 56. This causes an electrical signal to be transmitted along cables 33 to console 34, where the processor interprets the signal to activate the icon or menu. The tracking of a pointing device for a GUI is well known in the art, and is not described further here.

Similarly, physician 22 may move cursor 48 from a first position to a second position, in order to draw a corresponding line via the GUI from the first position to the second position, mark points using buttons 56, and otherwise interact with images and maps that are displayed on the display device.

Figure 4:
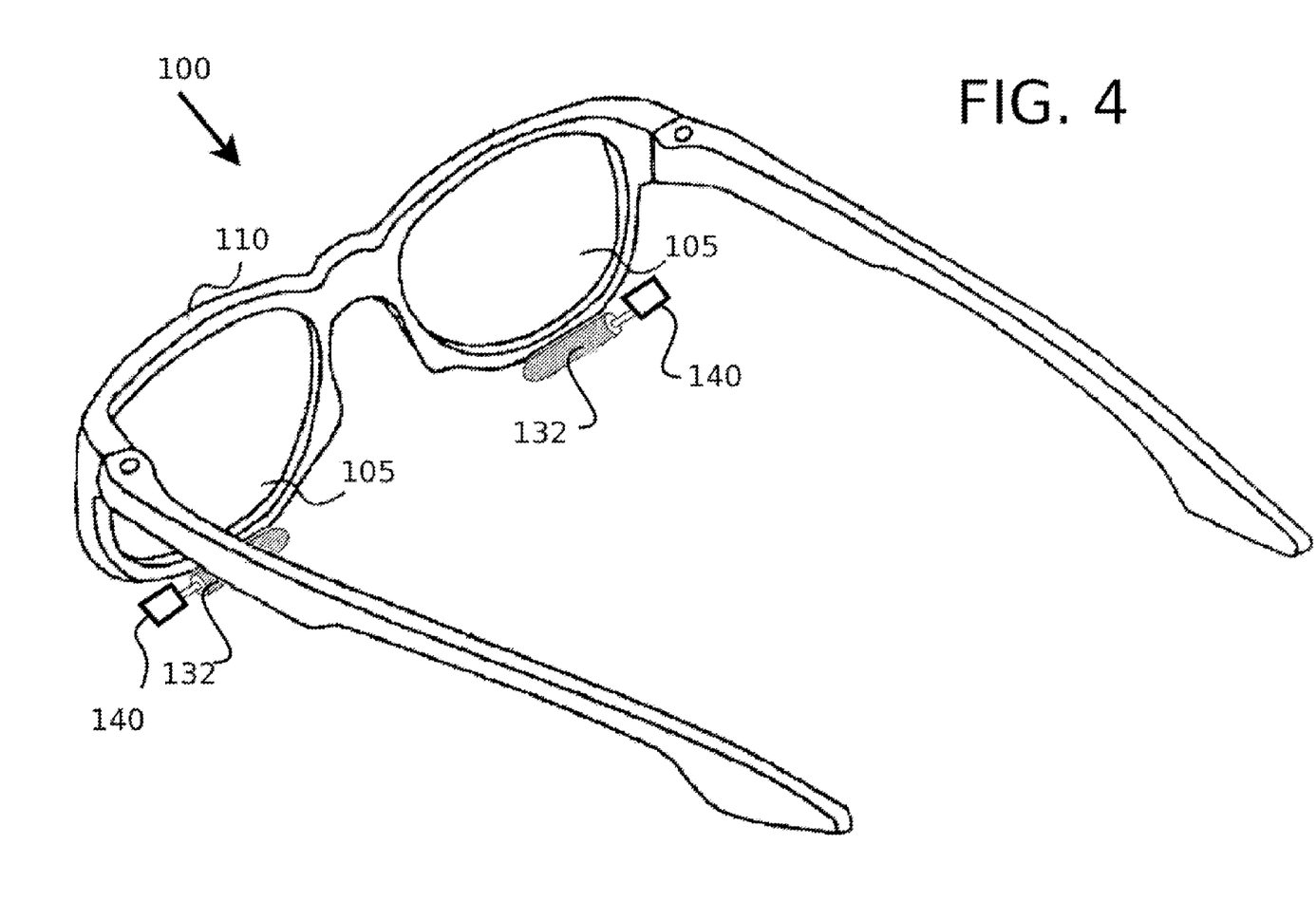
FIG. 4 is a pictorial illustration of a device that produces a virtual reality display that may be used in the system shown in FIG. 1, in accordance with another alternate embodiment of the invention.

In some embodiments of the invention, the images are displayed on a virtual reality display rather than a conventional display monitor. Reference is now made to FIG. 4, which is a pictorial illustration of a device that produces a virtual reality display, in accordance with an alternate embodiment of the invention.

Virtual reality goggles 100 comprise at least one, and typically two, display devices 105, supported by a frame 110, constructed so that physician 22 (FIG. 1) may wear goggles 100 with display devices 105 in front of his eyes. Display devices 105 show virtual images, for example, of a part of heart 24 (FIG. 1) and distal end 29 of catheter 23 (FIG. 2), as described herein below. Alternatively, display devices 105 may be transparent, or partially transparent, in order to provide augmented reality images in which the virtual images are superimposed on the body of subject 26 (FIG. 1).

Methods for display of virtual reality and augmented reality images are well known in the art. An exemplary disclosure is U.S. Pat. No. 6,695,779, issued to Sauer et al., which is incorporated herein by reference.

Goggles 100 comprise a position sensor 132, similar to position sensor 32, which senses magnetic fields produced by coils 31 (FIG. 1) and transmits, in response to the sensed fields, position-related electrical signals to console 34 (FIG. 1), using a wireless transmitter 140. Wireless transmitter 140 may also be used as a receiver for images to be displayed on display devices 105. Alternatively, the transmitter may be wired to the console.

Position sensor 132 is similar to position sensor 32, but may comprise a miniaturized position sensor, for example as described in U.S. Pat. No. 6,201,387, issued to Govari, which is incorporated herein by reference.

Alternatively, position sensor 132 may comprise a wireless position sensor. A suitable device is described in U.S. Patent Application Publication No. 2005/0099290, which is incorporated herein by reference. In this case, wireless transmitter 140 acts solely as a receiver for images from image processor 43 (FIG. 1).

Further alternatively, position sensor 132 may transmit signals to the console over a cable (not shown). However, this alternative is less convenient. Similarly, images to be displayed on display devices 105 may be received over cables (not shown). Because the positions of display devices 105 are fixed in relation to position sensor 132, system 20 is able to determine the positions of each of display devices 105. Using the information provided by the position sensor 132, the position processor 36 (FIG. 1) can register the virtual reality display with the body of the patient. In this manner, the operator can view an image of an organ superimposed on an image of the patient's body in the proper position and orientation, and can use the device 60 (FIG. 3) to interact with the images as described above.

Alternatively, as shown in FIG. 4, each of display devices 105 may be attached to its own position sensor 132. This allows greater flexibility of movement of the goggles, since the relative positions of display devices 105 need not be constant. Although FIG. 4 shows each position sensor 132 connected to a separate wireless transmitter 140, a single wireless transmitter 140 may be used.

The virtual reality image may be manipulated using many combinations of interface devices such as joystick 52 or interface device 60, as described above. As conditions of the medical procedure change, some embodiments may become less convenient than others. For example, some phases may be hazardous, e.g., taking place under conditions of radiation exposure, and requiring hands-off actuation of the medical instrument on the part of the physician 22. In such cases the use of goggles 100 may be preferable. In other situations, the lighting conditions in the operatory may be unsuitable for use of goggles 100.

In an alternate embodiment, position sensors 32, 54, 132 may be replaced by radiators, e.g., coils, that generate magnetic fields, which are received by sensors outside the subject's body. The external sensors generate the position-related electrical signals.

Figure 5:
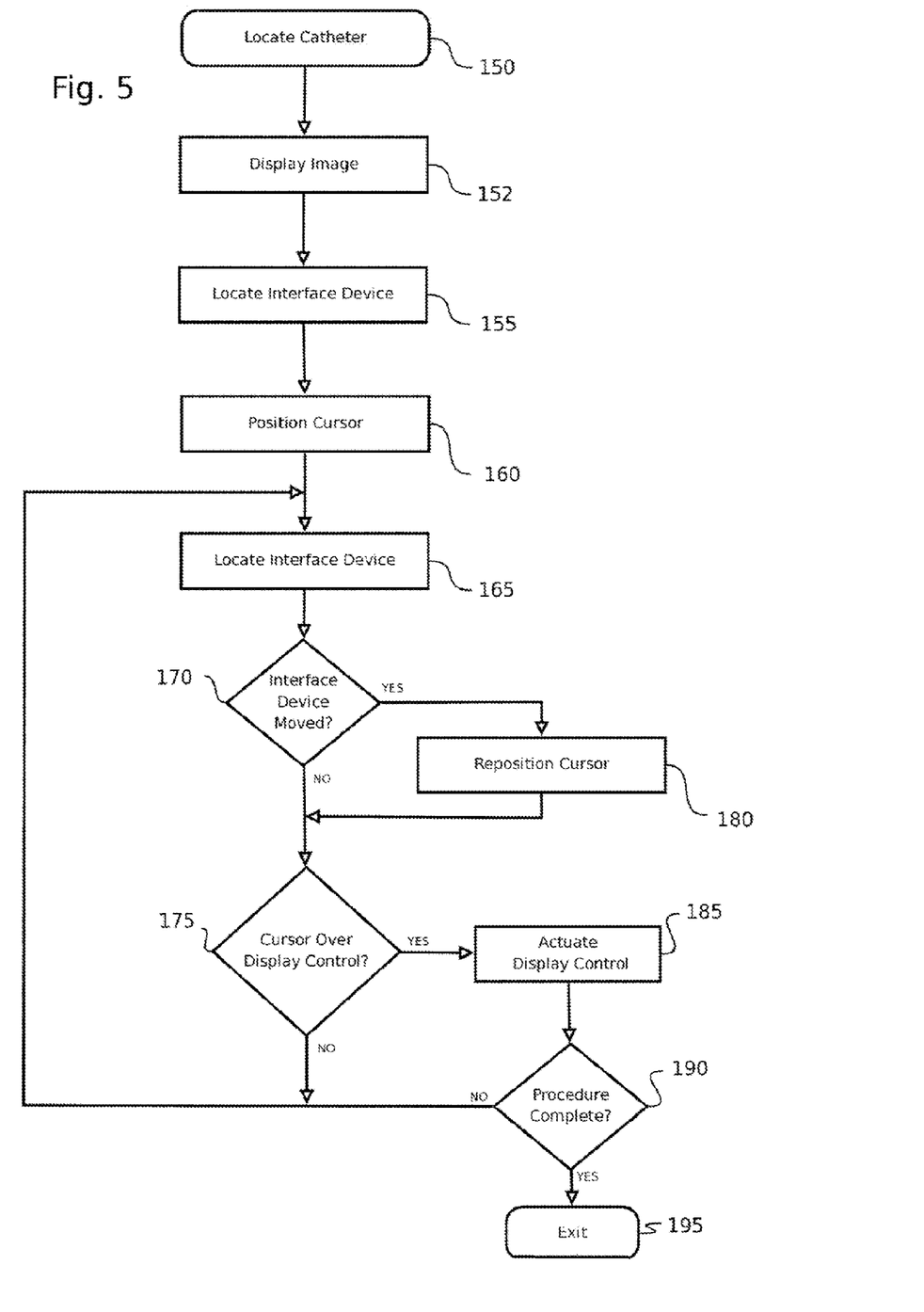
FIG. 5 is a flow chart showing a method for performing invasive medical operations with the assistance of a virtual touch screen, in accordance with a disclosed embodiment of the invention.

Reference is now made to FIG. 5, which is a flow chart showing a method for performing invasive medical operations with the assistance of a virtual touch screen, in accordance with a disclosed embodiment of the invention.

The method begins at an initial step 150, where the position of distal end 29 (FIG. 1) of catheter 23 is determined, typically using the magnetic fields produced by coils 31 and sensed by position sensor 32 (FIG. 2). Alternatively, as described above, the position of distal end 29 may be determined by external position sensors that detect magnetic fields generated at a fixed position relative to distal end 29.

Next, at step 152, an image, for example image 46, is acquired and displayed on display 44. The image may be an image of subject 26, which may be obtained, for example, using catheter 23. Alternatively, the image may be an image of distal end 29 overlaid on a representation of subject 26. Further alternatively, the image may show the position of distal end 29 with respect to a target within the subject. Steps 150 and 152 may be repeated as distal end 29 moves.

At step 155, typically performed concurrently with steps 150 and 152, the position of the interface device is determined, for example by position sensor 54 (FIG. 2). Alternatively, one of position sensors 32, 54 may be replaced by a radiator, which is used to as a reference establish coordinates for the system. In this case, the same external sensors are used to detect the positions of the distal end of the catheter and the interface device.

Next, at step 160, cursor 48 is positioned on display 44. The initial position may be predefined or random.

At step 165, typically performed after a time delay, or after an interrupt, the position of the interface device is determined, as in step 155.

Next, at decision step 170, it is determined whether the interface device has moved since the previous iteration of step 165, or step 155 if this is the first iteration. If the determination at determination step 170 is negative, then control proceeds to a decision step 175, described below.

If the determination at decision step 170 is affirmative, then control proceeds to step 180. Cursor 48 is repositioned on display 44 in response to the displacement of the interface device relative to its previous position. Control proceeds to decision step 175.

In some embodiments of the invention, display controls, for example a GUI as described above, appear on display 44. At decision step 175, it is determined whether the cursor is superimposed on one of the display controls. If the determination at decision step 175 is negative, then control returns to step 165.

If the determination at decision step 175 is affirmative, then control proceeds to step 185. The display control is actuated. This may cause a change in the orientation or scale of the image on display 44, or other changes to the display of the image or may actuate a function of catheter 23, according to a computer application that is controlled via the GUI.

Next at decision step 190, it is determined whether the procedure is complete. Typically, this is indicated by the actuation of an appropriate display control at step 185. If the determination at decision step 190 is negative, then control returns to step 165.

If the determination at decision step 190 is affirmative, then control proceeds to final step 195, where the method ends.

Figure 6:
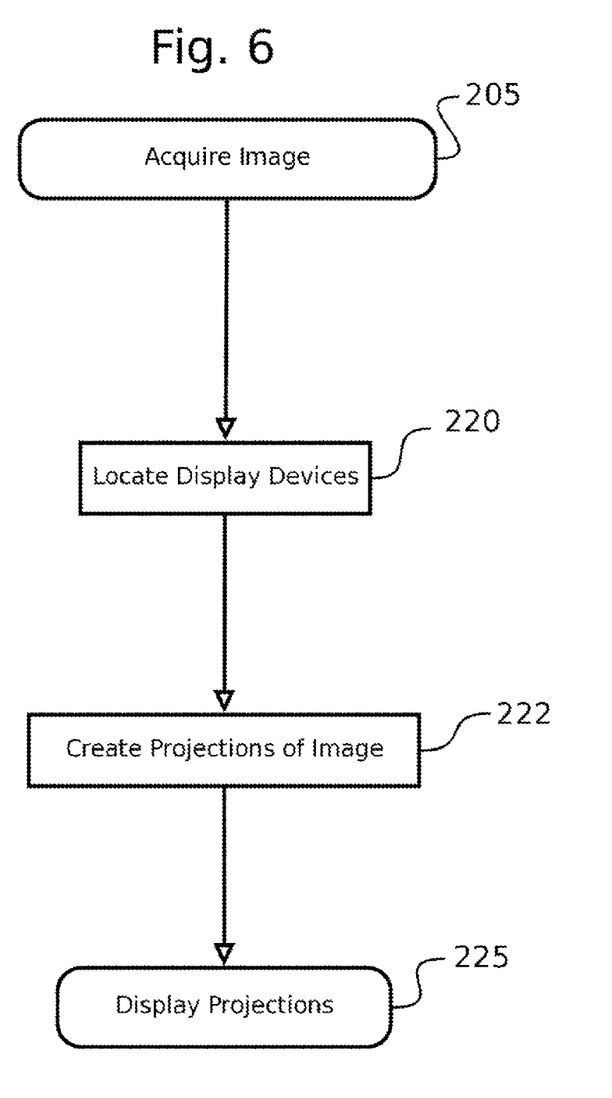
FIG. 6 is a flow chart showing a method for imaging an anatomical structure on the virtual reality display of FIG. 4, in accordance with a disclosed embodiment of the invention.

Reference is now made to FIG. 6, which is a flow chart showing a method for imaging an anatomical structure on the virtual reality display of FIG. 4, in accordance with a disclosed embodiment of the invention. The process steps are shown in a particular linear sequence in FIG. 6 for clarity of presentation. However, it will be evident that many of them can be performed in parallel, asynchronously, or in different orders. For example, acquiring the image and locating the display devices may be performed in either order, or simultaneously.

The method begins at initial step 205, where an image, typically three-dimensional, of a part of an anatomical structure is acquired. For an ultrasound image, this may be performed as described for example, in U.S. Patent Application Publication No. 2006/0241445, which is incorporated herein by reference.

Next, at step 220, one or more position sensors 132 (FIG. 4) determine the positions of display devices 105. The position information is transmitted to console 34.

Next, at step 222, image processor 43 uses position information from step 220 and standard geometrical techniques to obtain, for each of display devices 105, a 2-dimensional projection of the image.

At final step 225, the projections are transmitted to display devices 105 (FIG. 4) and displayed.

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art, which would occur to persons skilled in the art upon reading the foregoing description.

The invention claimed is:

1. Apparatus for invasive medical operations involving real time image processing in the body of a living subject, comprising:
   one or more field generating elements disposed at known locations for generating magnetic fields at respective frequencies;
   a medical instrument adapted for insertion into said body, the medical instrument comprising (i) a first magnetic position sensor coupled thereto that emits first signals responsively to said magnetic fields and (ii) and ultrasonic imaging sensor for imaging a target structure in the subject and emitting ultrasound signals, (iii) a handle on said medical instrument, (iv) an interface device comprising a joystick on the medical instrument, the joystick having a second magnetic position sensor coupled thereto that emits second signals responsively to said magnetic fields and (v) positioning controls for said medical instrument on the handle of said medical instrument, and wherein said joystick is attached to said handle;
   a position processor operative to receive said first signals and said second signals and to determine respective position information of said joystick and said medical instrument relative to said known locations, responsively to said first signals and said second signals;
   an image processor having an edge detection algorithm, the image processor using the respective position information of said joystick and said medical instrument and ultrasound signals of the ultrasonic imaging sensor and producing an image of the target structure in the subject;
   a display device operative to display the image of the target structure responsively to said position of said medical instrument; and
   a cursor moveable thereon under control of said position processor, movements of said cursor being controlled by said second magnetic position sensor responsively to changes in said position of said joystick, and wherein moving of the joystick continuously controls an edge threshold of the image of the target structure on the display using the edge detection algorithm.

2. The apparatus according to claim 1, wherein said display device has a display control that is actuated responsively to a superimposition of said cursor thereon.

3. The apparatus according to claim 1, wherein said display device has a display control that is actuated responsively to a displacement of said joystick generally toward said display device while said cursor is superimposed on said display control.

4. The apparatus according to claim 1, wherein said display device comprises a virtual reality display device having a third magnetic position sensor that emits third signals responsively to said magnetic fields.

5. The apparatus according to claim 1, wherein said first magnetic position sensor and said second magnetic position sensor comprise at least two sensor coils.

6. Apparatus for invasive medical operations involving real time image processing in the body of a living subject, comprising:
   a medical instrument adapted for insertion into an anatomical structure in said body, the medical instrument comprising (i) one or more first field generating elements for generating first magnetic fields at respective frequencies and (ii) an ultrasonic imaging sensor for imaging a target structure in the subject and emitting ultrasound signals, (iii) a handle on said medical instrument, (iv) an interface device comprising a joystick on the medical instrument, the joystick having one or more second field generating elements for generating second magnetic fields at respective frequencies and (v) positioning controls for said medical instrument on the handle of said medical instrument, and wherein said joystick is attached to said handle;
   a magnetic position sensor at a known location that emits first signals responsively to said first magnetic fields, and that emits second signals responsively to said second magnetic fields;
   a position processor operative to receive said first signals and said second signals and to determine respective positions information of said joystick and said medical instrument relative to said known location, responsively to said first signals and said second signals;
   an image processor having an edge detection algorithm, the image processor using the respective position information of said joystick and said medical instrument and ultrasound signals of the ultrasonic imaging sensor and producing an image of the target structure in the subject; and
   a display device operative to display the image of the target structure responsively to said position of said medical instrument;
   a cursor moveable thereon under control of said position processor, movements of said cursor being controlled by said position processor responsively to changes in said position of said joystick, and wherein moving of the joystick continuously controls an edge threshold of the image of the target structure on the display using the edge detection algorithm.

7. The apparatus according to claim 6, wherein said display device has a display control that is actuated responsively to a superimposition of said cursor thereon.

8. The apparatus according to claim 6, wherein said display device has a display control that is actuated responsively to a displacement of said joystick generally toward said display device while said cursor is superimposed on said display control.

9. The apparatus according to claim 6, wherein said display device comprises a virtual reality display device having one or more third field generating elements for generating third magnetic fields, said magnetic position sensor being responsive to said third magnetic fields.

10. The apparatus according to claim 6, wherein said display device is operative to draw a line from a first position to a second position on said display device when said cursor is moved from said first position to said second position.

11. The apparatus according to claim 6, wherein said magnetic position sensor comprises at least two sensor coils.

* * * * *